United States Patent [19]

Rolski

[11] 4,259,242
[45] Mar. 31, 1981

[54] METHOD OF PREPARING VINDESINE SULFATE

[75] Inventor: Stanislaw Rolski, Indianapolis, Ind.

[73] Assignee: Eli Lilly and Company, Indianapolis, Ind.

[21] Appl. No.: 102,505

[22] Filed: Dec. 11, 1979

Related U.S. Application Data

[63] Continuation-in-part of Ser. No. 949,595, Oct. 10, 1978.

[51] Int. Cl.³ .............................................. C07D 519/04
[52] U.S. Cl. .................................................. 260/244.4
[58] Field of Search ........................ 260/244.4; 546/51

[56] References Cited

U.S. PATENT DOCUMENTS 3,205,220  9/1965  Svoboda et al. ................... 260/244.4

OTHER PUBLICATIONS

Brown, et al., "Quantitative Chemistry" (1964), pp. 168–169.
Barnett, et al., J. Med. Chem., vol. 21, No. 1, pp. 88–91, 01/78.

*Primary Examiner*—Donald G. Daus
*Assistant Examiner*—Diana G. Rivers
*Attorney, Agent, or Firm*—James L. Rowe; Arthur R. Whale

[57] ABSTRACT

A method for preparing vindesine monosulfate, substantially free from hemisulfate and disulfate.

5 Claims, No Drawings

METHOD OF PREPARING VINDESINE SULFATE

CROSS-REFERENCE

This application is a continuation-in-part of my co-pending application Ser. No. 949,595 filed Oct. 10, 1978.

BACKGROUND OF THE INVENTION

Vindesine is disclosed in the copending application of Cullinan, and Gerzon, Ser. No. 828,693 filed Aug. 29, 1977, and is named therein as 4-desacetyl VLB C-3 carboxamide. The compound has the following structure

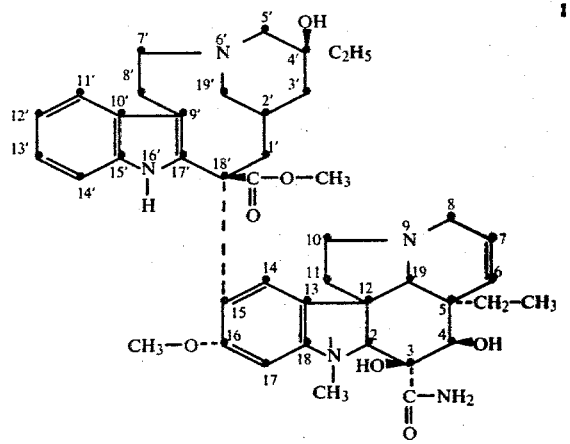

Vindesine can also be named as 4-desacetyl-3-descarbomethoxy VLB 3-carboxamide or as 23-amino-O⁴-desacetyl-23-demethoxy-vincaleukoblastine. A sulfate salt of vindesine is also specifically disclosed in Ser. No. 828,693. This sulfate is obtained by neutralization of vindesine base with dilute sulfuric acid followed by lyophilization. The salt thus obtained is electrostatic, hygroscopic and unstable upon storage.

It has now been found that there are three salts of vindesine formed with sulfuric acid. These salts are the hemisulfate, monosulfate and disulfate salts. The dissociation constant of sulfuric acid is such that, unless a strong base is present, the sole ionization of importance is

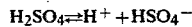

Vindesine has three basic groups, those at N-9, N-6 and N-1, but titration of vindesine shows only two titratable basic groups, probably at N-9 and N-6. In the monosulfate salt, probably one mole of bisulfate ($HSO_4^-$) and one mole of vindesine react, the salt forming on the most basic amine group. The hemisulfate is formed from one mole of sulfuric acid and two moles of vindesine. In the disulfate, two of the basic amine groups in vindesine react with bisulfate ions, giving a 1:2 ratio of base to acid.

In transplanted tumor systems in animals, vindesine has shown an activity approaching that of vincristine although potentially lacking some of the neurological side-effects which accompany the clinical use of the latter drug. Vindesine is now undergoing a world-wide clinical trial and so far appears in early tests to be active against certain leukemias and lymphomas, and against both small cell and non-small cell carcinomas, particularly in conjunction with cis-platinum.

Vinblastine and vincristine, two vinca alkaloids related to vindesine, now being marketed as oncolytic agents, are formulated as sulfate salts for use in intravenous administration to patients suffering from various neoplasms. The formulations are freeze dried and reconstituted by adding water just prior to use. In such a formulation, the drug should go into solution rapidly and completely. As previously stated, titration of vindesine base with dilute sulfuric acid and then evaporating the resulting solution to dryness yielded a salt which was electrostatic and hygroscopic (difficult to handle) and its stability was unsatisfactory on storage.

It is an object of this invention to provide a method for the preparation of a vindesine salt which yields a product of good shelf stability, which is easy to handle, and which reconstitutes rapidly in water to form a solution.

SUMMARY OF THE INVENTION

In fulfillment of the above and other objects, this invention provides a method for preparing vindesine sulfate of good stability comprising the slow addition of 2 equivalents of a 1 N aqueous sulfuric acid solution to a dilute solution containing 2 equivalents of vindesine base in acetonitrile. It is preferred to add the dilute sulfuric acid to the vindesine solution in dropwise fashion with adequate mixing. The rate of addition and degree of mixing becomes critical as the neutralization of the vindesine base nears completion.

In my novel process, the preparation of the sulfate salt of vindesine is preferably carried out in two steps. First, one equivalent of 1 N aqueous sulfuric acid is added slowly (dropwise with stirring) to a 1% vindesine solution (2 equivalents) in acetonitrile. After this addition has been completed, the resulting suspension is stirred for about ½ hour after which time the slow addition with stirring of a second equivalent of 1 N aqueous sulfuric acid is carried out. Stirring is then continued for an additional half-hour, at which time the precipitated vindesine monosulfate is separated by filtration. The filter cake is washed with the same organic solvent used to dissolve the vindesine base initially, and is then dried to a constant weight. The yield of sulfate from base is 94–96 percent.

More specifically, the 1 N aqueous sulfuric acid is added to a 1% solution of vindesine in acetonitrile at such a rate that the rate of addition of sulfuric acid to the vindesine solution coupled with a rate of stirring or degree of mixing serves to avoid the formation of vindesine disulfate. An addition rate of about 1 ml./min. has been found to be satisfactory, particularly towards the end of the neutralization process. A buret is conveniently employed for the addition.

In carrying out the above process, the chief product formed between vindesine base and the first equivalent of sulfuric acid is the hemisulfate (2 equivalents of vindesine per equivalent of sulfuric acid or 2 moles of vindesine per mole of sulfuric acid). The hemisulfate precipitates and can be separated by filtration. The second equivalent of sulfuric acid, which is next added at the same rate, converts the hemisulfate to the monosulfate (one mole of vindesine per mole of sulfuric acid or one equivalent of vindesine per equivalent of sulfuric acid). If the addition is too rapid, especially toward the end of the neutralization process, or if excess sulfuric acid is used, disulfate (one mole of vindesine per 2 moles of sulfuric acid or one equivalent of vindesine per two equivalents of sulfuric acid) is formed. In this event, any sulfuric acid that is tied up as disulfate leaves, by necessity, some vindesine present as hemisulfate. The hemisulfate is less stable than vindesine monosulfate. For example, at 25° C. for one month, vindesine hemisulfate has only 85.2% of initial potency, but vindesine monosulfate has 97.4% of initial potency. Thus, the slow addition process of this invention avoids disulfate formation and the presence of hemisulfate and yields vindesine monosulfate of satisfactory stability which is easy to handle for pharmaceutical formulations and reconstitutes readily for IV use. The vindesine monosulfate thus produced also has suitable physical properties for use as an analytical standard.

A titration curve for the neutralization of vindesine base with 1 N aqueous sulfuric acid carried out as above shows an inflection point at pH=6.5 corresponding to the formation of vindesine hemisulfate. Further titration with 1 N sulfuric acid causes the apparent pH of the solution to drop to a pH in the range 4.5–5.0.

While it is possible to follow the above neutralization with a pH meter, the endpoint has proved to be variable (4.5–5.0) and it is preferred that the calculated amount of sulfuric acid based upon the HPLC determination of vindesine base present be added rather than relying upon an endpoint determination. Alternatively, the pH can be followed during titration by diluting an aliquot of the neutralization mixture with water and measuring the pH as usual. A pH of 4.5 corresponding to monosulfate can be achieved readily using this procedure.

Addition of excess sulfuric acid causes the apparent pH to drop further as the monosulfate is converted to disulfate. The presence of disulfate in monosulfate yields, upon solution (10 mg/ml.) in water, a more acidic pH than a pure vindesine monosulfate solution would yield (pH=4.5). Vindesine disulfate upon solution in water (10 mg/ml.) has a pH=2.0. Microanalysis of the solid sulfate shows a higher percent of sulfur than 3.76%, the calculated amount for vindesine monosulfate.

Vindesine sulfate obtained by the above procedure is hydrated and contains from 4 to 5% water (about 2 moles) by a Karl Fisher determination. Thus, vindesine sulfate contains, per molecule, 1 mole of vindesine, 1 mole of sulfuric acid and 2 moles of water.

In carrying out the process of this invention, acetonitrile has been specified as the solvent of choice for dissolving vindesine for its neutralization by aqueous sulfuric acid. Acetone can also be used, but acetonitrile is preferred because vindesine monosulfate prepared in that solvent has better stability. Use of 1 N sulfuric acid and a 1% vindesine solution in acetonitrile (or acetone) has been specified since these concentrations have been found to be optimal. As will be apparent to those skilled in the art, manipulation of the above concentrations can produce vindesine monosulfate of satisfactory properties. Such operative processes would fall within the scope of this invention.

This invention is further illustrated by the following specific example.

EXAMPLE 1

A solution is prepared from 32.84 g. of vindesine base and 3284 ml. of acetonitrile. One equivalent of 1 N aqueous sulfuric acid is added thereto with stirring at the rate of about 1 ml./min. (1 g. of vindesine free base of 97 percent purity requires 1.25 ml. of 1.0 N aqueous sulfuric acid). After the first equivalent of sulfuric acid has been added, the resulting suspension (vindesine hemisulfate) is stirred at room temperature for a period of from 20 to 30 minutes, after which time the second equivalent of 1 N aqueous sulfuric acid is added at the same rate with stirring. During the addition of the second equivalent of sulfuric acid, the hemisulfate formed by the addition of the first equivalent of sulfuric acid is converted to vindesine monosulfate. After the second equivalent of sulfuric acid has been added, the resulting suspension is stirred for an additional 30 minutes at ambient temperature. Vindesine sulfate thus prepared is next filtered and the filter cake washed with 100 ml. acetonitrile. The precipitate is dried in vacuo at a temperature not exceeding 35° C. to constant weight; yield=34.8–35.6 g. (94–96%).

In the above example, the rate of addition of dilute sulfuric acid to the vindesine base or vindesine suspension solution was 1 ml./min. About 0.1 moles of vindesine base were thus neutralized per minute. Slower rates of addition give substantially the same results. More rapid rates of addition can be utilized provided that stirring is sufficient to insure that the formation of disulfate is avoided. What is important is not the absolute rate of addition of the dilute aqueous sulfuric acid, but addition at a suitable rate coupled with adequate stirring such as to minimize disulfate formation, especially toward the end of the neutralization process.

The above procedure can be carried out in two steps; i.e., the hemisulfate, which is a well-characterized compound, can be isolated, dried and then resuspended in acetonitrile or acetone for the second equivalent of sulfuric acid to be added to the suspension.

Vindesine monosulfate thus prepared by conventional procedures is loaded into ampoules where it is kept in a form suitable for dissolving in water for IV administration. Prior to use, the ampoule is opened and the required amount of physiological saline added to the vindesine monosulfate to give a solution suitable for IV injection in the treatment of the various neoplasmas against which vindesine has been found to be active.

I claim:

1. The process of preparing a stable, rapidly soluble sulfate salt of vindesine suitable for use in intravenous administration which comprises the steps of dissolving substantially pure vindesine base in acetonitrile or acetone at a concentration of about 1% and then adding thereto an equivalent amount of 1 N aqueous sulfuric acid with stirring at a rate such as to minimize formation of vindesine disulfate to yield a product which is substantially pure vindesine monosulfate.

2. A process according to claim 1 in which the solvent is acetonitrile.

3. A process according to claim 1 in which the 1 N aqueous sulfuric acid is added at the rate of 1 ml. per min. or slower.

4. A process according to claim 1 in which vindesine base is neutralized at the rate of 0.01 moles per minute or slower.

5. The process of preparing a stable, rapidly water soluble sulfate salt of vindesine suitable for use in intravenous administration which comprises the steps of dissolving two equivalents vindesine base in acetonitrile or acetone at a concentration of about 1% and then adding thereto one equivalent of 1 N aqueous sulfuric acid with stirring so as to form vindesine hemisulfate and then adding a second equivalent of 1 N aqueous sulfuric acid thereto with stirring to convert the vindesine hemisulfate to vindesine monosulfate at such a rate as to minimize the formation of vindesine disulfate, to yield a product which is substantially pure vindesine monosulfate as the dihydrate.

* * * * *